United States Patent
Husain et al.

(10) Patent No.: US 10,198,566 B2
(45) Date of Patent: Feb. 5, 2019

(54) COERCION RESISTANT AUTHENTICATION SYSTEM BASED ON NEUROPHYSIOLOGICAL RESPONSES TO MUSIC

(71) Applicant: Cal Poly Pomona Foundation, Inc., Pomona, CA (US)

(72) Inventors: Mohammad I. Husain, Diamond Bar, CA (US); Max Wolotsky, Laguna Niguel, CA (US)

(73) Assignee: CAL POLY POMONA FOUNDATION, INC., Pomona, CA (US)

( * ) Notice: Subject to any disclaimer, the term of this patent is extended or adjusted under 35 U.S.C. 154(b) by 110 days.

(21) Appl. No.: 15/434,967

(22) Filed: Feb. 16, 2017

(65) Prior Publication Data
US 2017/0242994 A1 Aug. 24, 2017

Related U.S. Application Data

(60) Provisional application No. 62/298,016, filed on Feb. 22, 2016.

(51) Int. Cl.
*G06F 21/32* (2013.01)
*G06F 21/55* (2013.01)
(Continued)

(52) U.S. Cl.
CPC ............ *G06F 21/32* (2013.01); *A61B 5/01* (2013.01); *A61B 5/021* (2013.01); *A61B 5/024* (2013.01);
(Continued)

(58) Field of Classification Search
CPC . G06F 21/32; G06F 21/55; A61B 5/01; A61B 5/021; A61B 5/024; A61B 5/0476; A61B 5/0531; A61B 5/0816; A61B 5/117
(Continued)

(56) References Cited

U.S. PATENT DOCUMENTS 9,596,236 B2 * 3/2017 Dunn ................... H04L 63/0861
2007/0198850 A1 * 8/2007 Martin ............... G07C 9/00087
713/186
(Continued)

OTHER PUBLICATIONS

Gibson, et al, "Musipass: Authenticating Me Softly with "My" Song", (2009), Proceedings New Security Paradigms Workshop. all pages. (Year: 2009).*
Wolotsky, et al, "Chill-Pass : Using Neuro-Physiological Responses to Chill Music to Defeat Coercion Attacks", May 3, 2016, arXiv, all pages (Year: 2016).*

*Primary Examiner* — Michael S McNally
(74) *Attorney, Agent, or Firm* — Greenberg Traurig LLP

(57) ABSTRACT

The present invention discloses a method and system for authentication that is coercion resistant by using music that invokes reproducible neurological responses uniquely to a user in order to authenticate the user. The neurological responses may include neurochemical activities inside the brain and brain waves. The unique neurological response of a user to his or her selected music is stimulated by neurochemical release such as dopamine. During the most pleasing part of the music, the user's neurochemical activities and brain waves notably change, which can be captured by using sensors. The timing, rate and extent of the notable change in neurological responses can be used to form a user's unique and non-transferable password. The present invention can be used to authenticate a user while preventing against standard attacks as well as coercion attack, i.e., forcing the user to provide his or her authentication material such as a password.

6 Claims, 2 Drawing Sheets

(51) Int. Cl.
*A61B 5/117* (2016.01)
*A61B 5/0476* (2006.01)
*A61B 5/01* (2006.01)
*A61B 5/021* (2006.01)
*A61B 5/024* (2006.01)
*A61B 5/053* (2006.01)
*A61B 5/08* (2006.01)

(52) U.S. Cl.
CPC .......... *A61B 5/0476* (2013.01); *A61B 5/0531* (2013.01); *A61B 5/0816* (2013.01); *A61B 5/117* (2013.01); *G06F 21/55* (2013.01); *G06F 2221/034* (2013.01)

(58) Field of Classification Search
USPC ............................................................ 726/6
See application file for complete search history.

(56) References Cited

U.S. PATENT DOCUMENTS

| | | | | |
|---|---|---|---|---|
| 2014/0337634 | A1* | 11/2014 | Starner | ................ H04L 9/3231 |
| | | | | 713/186 |
| 2015/0358790 | A1* | 12/2015 | Nasserbakht | ..... G06F 17/30088 |
| | | | | 455/414.1 |
| 2018/0234244 | A1* | 8/2018 | Starner | ................ H04L 9/3231 |

* cited by examiner

COERCION RESISTANT AUTHENTICATION SYSTEM BASED ON NEUROPHYSIOLOGICAL RESPONSES TO MUSIC

RELATED APPLICATION

This application claims the benefit of priority under 35 U.S.C. § 119(e) to Provisional Application No. 62/298,016, filed on Feb. 22, 2016, which is incorporated by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

THE NAMES OF THE PARTIES To A JOINT RESEARCH AGREEMENT

Not applicable.

BACKGROUND OF THE INVENTION

Alphanumeric and biometric (e.g., fingerprints) authentications are common and popular. While it is possible to copy alphanumeric and biometric information, it is not always trivia to do so. It is often easier to simply force a user into authenticating a system. Current alphanumeric and biometric authentication systems cannot withstand situations where a user is forced to release their passwords under hostile circumstances. Coercion attacks are considered dangerous because most authentication systems cannot protect against users who attempt to authenticate themselves after being put under significant stress, such as under physical threat. Coercion attacks can undermine cryptography and prove even the most secure alphanumeric or biometric authentication systems worthless.

Coercion attacks are effective because they allow an attacker to acquire authentication materials from a victim, regardless of if those materials are something they know, something they have, or something they are. The reason being that something you know can be told to another, something you have can be given to another, and something you are can be seen by another. Because these extra factors can be transferred to an attacker, or in the case of biometrics copied by an attacker, they are not effective in the scenario where a victim is coerced into giving up their authentication materials to the attacker. To combat this issue, we propose a coercion resistant authentication system ("CRAS") that could prevent authentication under significant stress and offer at least the same protections as biometric and alphanumeric passwords.

Music may result in a release of neurochemical, such as dopamine, inside the brain of a user who listens to the music. The dopamine release results in one or more neurophysiological responses from the user, such as change of heart rate, skin conductance, skin temperature, blood pressure, respiration rate, and Alpha/Beta/Gamma/Delta/Theta brave waves. Not all music, however, would stimulate a dopamine release in a user; and a piece of music does not necessarily stimulate the same dopamine release in every user. The degree of neurophysiological responses caused by a dopamine release varies from user to user as well as the music being listened to. Because of the uniqueness of the neurophysiological response of a user to a particular piece of music, such unique neurophysiological response may be use as a key for authentication.

The dopamine release stimulated by listening to highly pleasurable music is often. referred to as the "chill effect." This is because the most common description of such a reaction is feeling a "chill" or "shivers down the spine." The chill effect may be mathematically defined based on a pre-defined magnitude and/or occurrence of neurophysiological responses. A music piece is considered a "chill" music if a chill effect is found in multiple occurrences during listening to that piece of music. As previously discussed, not all music would stimulate a dopamine release in a user; similarly, not all music would stimulate a chill effect in a user, Moreover, not all segments of a music piece that could stimulate a chill effect would result in sufficient magnitude of neurophysiological responses suitable for use in a CRAS. Therefore, a screening process is necessary to determine specific segment(s) of a music piece that would he suitable for use in a CRAS.

BRIEF SUMMARY OF THE INVENTION

The present invention relates to an authentication method and system that uses music (e.g. a sound perceived as pleasingly harmonious that invokes one or more reproducible neurophysiological responses) in order to authenticate a user. Such neurophysiological responses include, but are not limited to, heart rate, skin conductance, skin temperature, blood pressure, respiration rate, and Alpha/Beta/Gamma/Delta/Theta brave waves. The neurophysiological responses of a user to music are stimulated by neurochemical release such as dopamine. When listening to certain selected part(s) of the music, the user's physiological responses, neurochemical activities, and neurological responses (such as brain waves) notably change, which can be captured by sensors. The timing, rate and extent of the notable change in neurophysiological responses can then be used to form the user's unique non-transferable password. The present invention can be used to authenticate a user uniquely while preventing against standard attacks (attacks already addressed by existing authentication systems) as well as coercion attack.

It is an objective of this invention to provide a method and system for authentication that will not allow authentication under significant stress.

It is a further objective of this invention to provide an authentication process using a user's neurophysiological responses to a selected music piece.

These and other objectives are preferably accomplished by providing a method and system comprising one or more sensors configured to sense and collect one or more neurophysiological responses from a user, a memory configured to store a plurality of music pieces and to record and store the neurophysiological responses, an audio module configured to play the plurality of music pieces, and a processor configured to determine chill effect based on the neurophysiological responses and one or more pre-determined criteria (also referred to as chill response). The sensors are attached to a user to sense and collect the user's neurophysiological responses when the user listens to a selected music piece. The processor identifies whether or not a chill effect exists based on the user's neurophysiological responses, When a chill effect is identified, the corresponding neurophysiological responses may be used as an authentication material for the user.

These and other aspects of this invention will become apparent to those skilled in the art after reviewing the following description of the invention.

BRIEF DESCRIPTION OF THE SEVERAL VIEWS OF THE DRAWINGS

The above-mentioned features and objects of the present disclosure will become more apparent with reference to the following description taken in conjunction with the accompanying drawings and images wherein like reference numerals denote like elements and in which.

DETAILED DESCRIPTION OF THE INVENTION

For illustrative purpose, the principles of the present invention are described by referring to an exemplary embodiment thereof. Before any embodiment of the invention is explained in detail, it should be understood that the invention is not limited in its application to the details of construction and the arrangement of components set forth in the following description or illustrated in the following drawings. The invention is capable of other embodiments and of being practiced or of being carried out in various ways. Also, it should be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
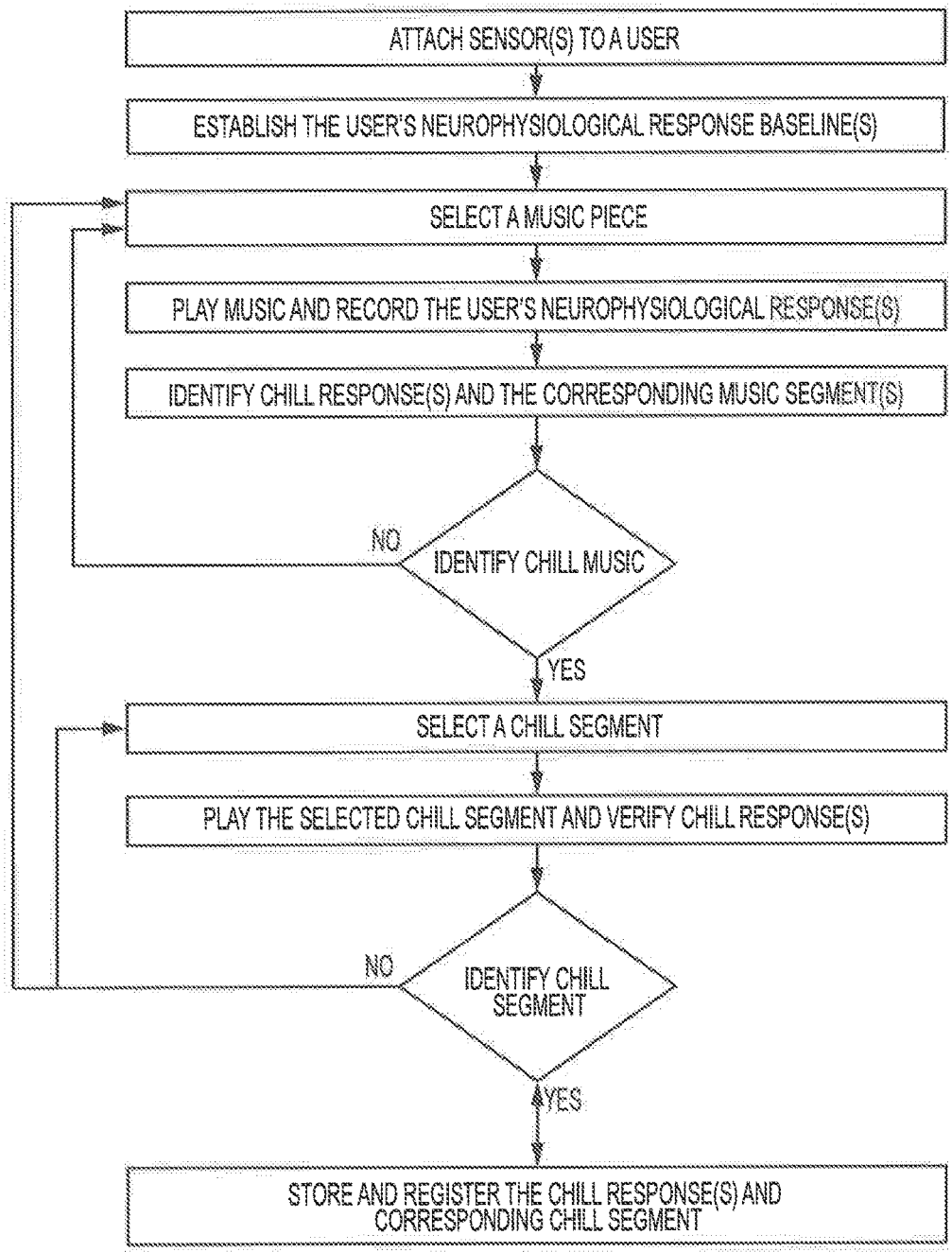
FIG. 1 is a flow diagram of a process for identifying and registering neurophysiological responses(s) stimulated by listening to selected chill music segment.

A screening process is necessary to determine specific segment(s) of a music piece that would be suitable for use in the present invention, in one embodiment, as shown in FIG. 1, one or more sensors are attached to a user to sense the user's neurophysiological responses. The user is initially placed under the user's comfortable state in order to establish the user's neurophysiological response baselines (i.e., the user's neurophysiological responses under ordinary circumstances and without external stimulus). One or more sensor(s) sense and establish the user's neurophysiological response baselines. A music piece is then selected and played for the user to listen to, and the sensors sense and collect the user's neurophysiological responses to the music. The music piece should not be linked to a specific memory of the user, for instance, some music lyrics are linked to life events of a user, and such linkage may make the user's reaction to the music inconsistent or day-dependent (i.e., reaction varies from day to day). In one embodiment, the music piece is non-lyrical or contains lyrics that are not easily memorable.

Whether the user's neurophysiological responses to the music are deemed chill responses are then determined. A user's chill response refers to the deviation of the user's neurophysiological responses from the user's neurophysiological response baselines based on one or more pre-determined criteria. In one embodiment, a chill response is defined mathematically as any range of responses where every point in the range is greater than one standard deviation away from the average of the user's neurophysiological response baselines; and the range of responses must be no less than a pre-determined temporal duration (e.g., 5 seconds) in order to eliminate abnormal spikes of the listener's neurophysiological responses.

For a music piece to be a chill music for a user, there must exist multiple occurrences of chill responses from the user resulting from the user listening to the music piece. Each occurrence of chill responses would correspond to a segment of the music piece (i.e., chill responses occurring during the play of a segment of the music piece), and be identified. A chill segment refers to such a music segment with a corresponding chill response. If the selected music piece does not qualify as a chill music, then another music piece may be selected and the same process is applied in order to determine whether the later selected music piece qualifies as a chill music.

Once a chill music is identified, a chill segment may be selected. A chill segment may be manually selected by the user or automatically selected based on a pre-determined criterion. In one embodiment, the user may manually identify a segment from the chill music where a chill response occurs; then add time durations (e.g., 30 seconds) before and after mid-point of the segment and chose the finished segment as the user's chill segment. In another embodiment, an analysis software program may be used to parse the collected chill responses from a user listening to a complete chill music, compare the segments of the chill music where the user's chill responses occurred. The analysis program then determines the segment with the longest chill responses. A chill segment is then chosen by adding pre-determined time durations (e.g., 30 seconds) before and after the mid-point the segment with the longest chill responses. In one embodiment, if the program generated chill segment is not satisfactory, the pre-determined time duration may be adjusted to generate another chill segment, or the program may select another segment with chill responses and repeat the same process; or in some embodiment, the program may select another chill music and repeat the chill segment selection process.

Figure 2:
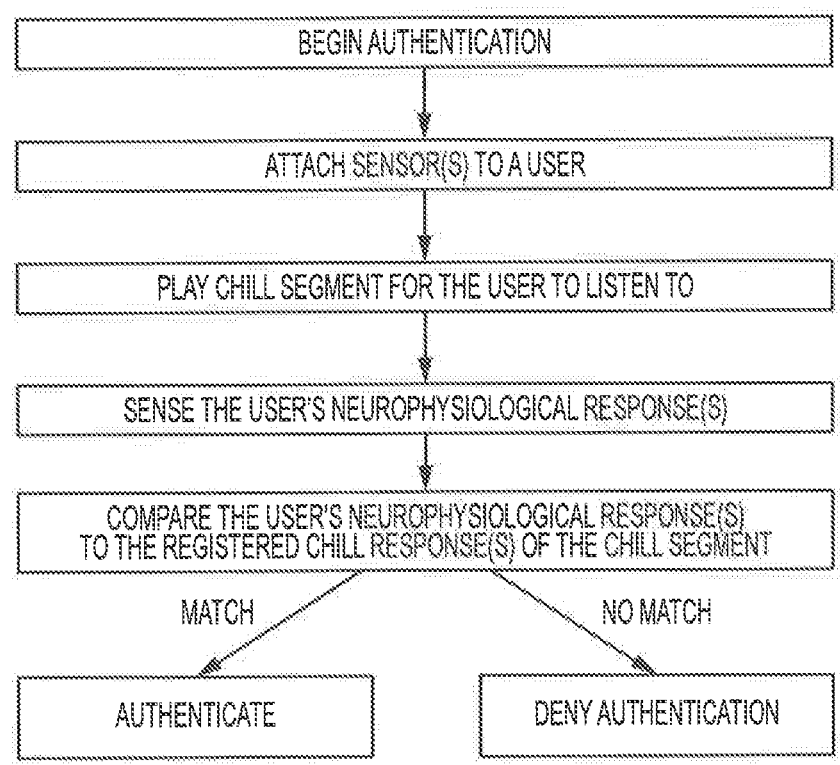
FIG. 2 is a flow diagram of an authentication process using neurophysiological responses(s) stimulated by listening to a selected music segment.

FIG. 2 is a flow diagram of an authentication process using neurophysiological responses(s) stimulated by listening to a selected music segment. As discussed above, chill music segment(s) and the corresponding neurophysiological responses are stored and registered in a memory or database for authentication purpose. As shown in FIG. 2, in one embodiment, an authentication process includes attaching one or more sensors to a user to be authenticated, playing a selected chill music segment for the user to listen to. The sensors will detect the user's neurophysiological responses when the user listens to the selected chill music segment. The user is authenticated if the user's neurophysiological responses match the registered neurophysiological responses stored in the memory or database.

The previous description of the disclosed examples is provided to enable any person of ordinary skill in the art to make or use the disclosed methods and apparatus. Various modifications to these examples will be readily apparent to those skilled in the art, and the principles defined herein may be applied to other examples without departing from the spirit or scope of the disclosed method and apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope. Skilled artisans may implement the described functionality in varying ways for each particular application, but such implementation decisions should not be interpreted as causing a departure from the scope of the disclosed apparatus and methods. The steps of the method or algorithm may also be performed in an alternate order from those provided in the examples.

The invention claimed is:

1. An authentication method comprising:
    establishing an average neurophysiological response baseline of a first user based on a first set of neurophysiological responses collected from the first user while the first user is in a state without external stimulus;
    causing to select a music piece;
    playing the music piece for the first user to listen to;
    collecting a second set of neurophysiological responses from the first user during the play of the music piece;
    the second set of neurophysiological responses comprising at least two neurophysiological responses wherein each of the at least two neurophysiological responses lasts longer temporally than a first pre-determined temporal duration, and each of the at least two neurophysiological responses deviates from the average neurophysiological response baseline by a pre-determined deviation amount;
    selecting a first neurophysiological response from the at least two neurophysiological and identifying a middle temporal point of a first portion of the music piece that corresponds to the first neurophysiological response;
    determining a second portion of the music piece having a second pre-determined temporal duration that ends at the middle temporal point, and a third portion of the music piece comprising a third pre-determined temporal duration that begins at the middle temporal point, wherein the cumulative temporal duration of the second and third pre-determined temporal durations temporally longer than the first neurophysiological response; and
    determining a chili music segment comprising the second portion of the music piece and the third portion of the music piece.

2. The authentication method of claim 1 wherein the music piece is non-lyrical.

3. The authentication method of claim 1 wherein the first pre-determined temporal duration is no less than 5 seconds.

4. The authentication method of claim 1 wherein the pre-determined deviation amount is no less than one standard deviation.

5. The authentication method of claim 1 wherein the first neurophysiological response lasts longer temporally than other neurophysiological responses of the at least two neurophysiological responses.

6. The authentication method of claim 1 further comprising:
    playing the chill music segment for a second user to listen to;
    collecting the second user's neurophysiological responses during the play of the chill music segment; and
    comparing the second user's the second user's neurophysiological responses during the play of the chill music segment to the first neurophysiological response.

* * * * *